United States Patent
Wittmann et al.

(10) Patent No.: US 9,140,644 B2
(45) Date of Patent: Sep. 22, 2015

(54) METHOD AND APPARATUS FOR DETECTING A GAS CONCENTRATION WITH REDUCED PRESSURE DEPENDENCY

(75) Inventors: Andreas Wittmann, Giswil (CH); Stefan Manzeneder, Sachseln (CH); Rui Protasio, Lucerne (CH); Michel Studer, Lucerne (CH); Thomas Hessler, Sachseln (CH)

(73) Assignee: Axetris AG, Kagiswil (CH)

( * ) Notice: Subject to any disclaimer, the term of this patent is extended or adjusted under 35 U.S.C. 154(b) by 599 days.

(21) Appl. No.: 13/462,026

(22) Filed: May 2, 2012

(65) Prior Publication Data

US 2012/0283961 A1  Nov. 8, 2012

(30) Foreign Application Priority Data

May 3, 2011 (EP) .................... 11401506

(51) Int. Cl.
- *G06F 19/00* (2011.01)
- *G01N 21/61* (2006.01)
- *G01N 21/39* (2006.01)

(52) U.S. Cl.
CPC .......... *G01N 21/39* (2013.01); *G01N 2021/399* (2013.01)

(58) Field of Classification Search
CPC .......... G01N 2021/1704; G01N 21/05; G01N 21/1702; G01N 21/33; G01N 33/0039; G01N 2021/399; G01N 21/39
USPC .......... 702/24, 25, 40, 57, 66, 70, 71, 73, 75, 702/76, 98, 106, 138, 47, 159; 73/21.03, 73/4.02; 356/437
See application file for complete search history.

(56) References Cited

U.S. PATENT DOCUMENTS

| | | | | |
|---|---|---|---|---|
| 7,069,769 B2* | 7/2006 | Kung | ............ | 73/24.02 |
| 7,508,521 B2* | 3/2009 | Liu et al. | ............ | 356/437 |
| 2010/0089117 A1 | 4/2010 | Liu et al. | | |

FOREIGN PATENT DOCUMENTS

| | | |
|---|---|---|
| EP | 0 995 984 A1 | 4/2000 |
| WO | 2008/112955 A1 | 9/2008 |

OTHER PUBLICATIONS

McGettrick et al., "Tunable Diode Laser Spectroscopy With Wavelength Modulation: Calibration-Free Measurement of Gas Compositions at Elevated Temperatures and Varying Pressure", Journal of Lightwave Technology, IEEE Service Center, New York, NY, US, vol. 27, No. 15, Aug. 1, 2009, pp. 3150-3161, XP011268383 (Previously listed in IDS submitted on May 2, 2012 with application).

(Continued)

*Primary Examiner* — John H Le
(74) *Attorney, Agent, or Firm* — Renner, Otto, Boisselle & Sklar, LLP

(57) ABSTRACT

This invention relates to a method that makes the measurement of a trace gas concentration invariant or at least less affected to pressure variations in the gas and atmospheric pressure changes. This method neither requires a pressure sensor nor a pressure calibration routine. Furthermore, the method can be applied to other gas species present in the background gas or to the background gas itself that cross-interfere with the target gas of interest. This allows removing any pressure dependency of cross-interference parameters of other gas species and/or the background gas. The new method for accurately measuring a gas concentration is based on optimizing the wavelength modulation amplitude of the laser to minimum pressure dependency.

17 Claims, 14 Drawing Sheets

(56) References Cited

OTHER PUBLICATIONS

McGettrick et al., "Tunable Diode Laser Spectroscopy With Wavelength Modulation: A Phasor Decomposition Method for Calibration-Free Measurements of Gas Concentration and Pressure", Journal of Lightwave Technology, IEEE Service Center, New York, NY, US, vol. 26, No. 4, Feb. 15, 2008, pp. 432-440, XP011204247 (Previously listed in IDS submitted on May 2, 2012 with application).

Stewart et al., "Recovery of Absolute Gas Absorption Line Shapes Using Tunable Diode Laser Spectroscopy with Wavelength Modulation Part I: Theoretical Analysis", Journal of Lightwave Technology, IEEE Service Center, New York, NY, US, vol. 29, No. 6, 1 Mar. 2011, pp. 811-821, XP011349098 (Previously listed in IDS submitted on May 2, 2012 with application).

European Search Report for corresponding European Application No. EP 11 40 1506 Issued Sep. 19, 2011.

McGettrick et al., "Tunable Diode Laser Spectroscopy With Wavelength Modulation: Calibration-Free Measurement of Gas Compositions at Elevated Temperatures and Varying Pressure", Journal of Lightwave Technology, IEEE Service Center, New York, NY, US, vol. 27, No. 15, Aug. 1, 2009, pp. 3150-3161, XP011268383.

McGettrick et al., "Tunable Diode Laser Spectroscopy With Wavelength Modulation: A Phasor Decomposition Method for Calibration-Free Measurements of Gas Concentration and Pressure", Journal of Lightwave Technology, IEEE Service Center, New York, NY, US, vol. 26, No. 4, Feb. 15, 2008, pp. 432-440, XP011204247.

Stewart et al., "Recovery of Absolute Gas Absorption Line Shapes Using Tunable Diode Laser Spectroscopy with Wavelength Modulation Part I: Theoretical Analysis", Journal of Lightwave Technology, IEEE Service Center, New York, NY, US, vol. 29, No. 6, Mar. 1, 2011, pp. 811-821, XP011349098.

\* cited by examiner

METHOD AND APPARATUS FOR DETECTING A GAS CONCENTRATION WITH REDUCED PRESSURE DEPENDENCY

CROSS-REFERENCE TO RELATED APPLICATION

The present application claims priority under 35 USC §119 to European Patent Application No. 11 401 506.8 filed May 3, 2011, the entire disclosure of which is incorporated herein by reference.

TECHNICAL FIELD OF THE INVENTION

This invention relates to a method that reduces the dependency of a trace gas concentration measurement on pressure variations in the gas and atmospheric pressure changes, which can be applied to the targeted trace gases in background gases and to other gas species cross-interfering with the target gas as well. The invention pertains to an apparatus for the appliance of said method too.

DESCRIPTION OF THE RELATED ART

Industry and trade often require precise measurements of trace gases to ensure that concentrations of such trace gases are within acceptable limits. Compliance with these limits in turn can be used to verify factors such as whether the delivered gases meet certain purity limits and/or whether emissions of such gases comply with environmental regulations. Typical applications like process control, emission and environmental monitoring, safety and air conditioning require precise concentration measurements. Wavelength modulation spectroscopy (WMS) is a way to enhance the sensitivity of gas measurements, especially important, when small concentration shall be measured. For example, monitoring of $NH_3$ slip in de-$NO_x$ processes based on Selective Catalytic Reduction (SCR). In power generation, $NO_x$ can be reduced by up to 99% with SCR where $NH_3$ is injected into the exhaust gas. This process has found its way into emission control of truck and car diesel engines. In this application, ammonia slip can occur. This requires a sensitivity of the sensor of 1 ppm $NH_3$ or better, which is measured in the exhaust gas. However, pressure variations in the gas affect the harmonic measurement signal and, as a consequence, result in inaccuracy of the concentration measurement.

In wavelength modulation spectroscopy (WMS) the wavelength of the laser source is modulated in a certain wavelength range which allows covering an absorption feature of the target gas(es). In case of using diode lasers, modulation is achieved by varying the laser current which results in a wavelength and intensity modulation of the emitted light. After the gas volume the light is incident on a detector and the electric signal is demodulated by a lock-in amplifier at the fundamental modulation frequency or a higher harmonic frequency. The following description below is focused on the second harmonic frequency 2f of the fundamental modulation frequency f, but applies analogous to other harmonics nf, with integer multiples n.

From the demodulated signal a concentration equivalent value is retrieved as for example the peak-height or the peak-valley height of the demodulated signal versus wavelength. In order to be independent of laser power fluctuations, the demodulated signal can be divided by a dc-value of the detector. For this dc-value the detector signal can be averaged before the lock-in detector or the dc-component of the lock-in can be used.

In order to increase the signal-to-noise ratio, state-of-the-art approaches optimize the wavelength modulation amplitude for maximum signal. The maximum signal is reached for a certain modulation index, which is defined as a multiple of the full-width at half-maximum (FWHM) of the absorption line. Wavelength modulation spectroscopy (WMS) is very sensitive to changes in the modulation index. Since the FWHM of the gas is inversely proportional to the pressure, a change of pressure will result in a change of the modulation index (by working at a fixed wavelength modulation amplitude) and as a consequence, in inaccuracy in the measured gas concentration.

The prior art shows a multitude of devices and methods for measuring the gas concentration of a target gas more or less precisely. Concerning precise measurements at changing pressure conditions, for example the patent document WO 2008/112955A1 by Xiang et al. discloses such a device and method. Said invention proposes an apparatus for detecting a concentration of a trace target gas in a sample gas comprising a light source, for example a tunable diode laser, for emitting light at a wavelength corresponding to an absorption line of the target gas, means operatively connected to said light source for modulating the wavelength of the emitted light and a light detector positioned to detect the intensity of light emitted from the light source that has passed through the sample gas at a multiple of the modulation frequency of the light source. Moreover the apparatus comprises a pressure sensor for detecting the pressure of the sample gas and a control unit coupled to the detector, the pressure sensor, and the light source, said control unit being arranged to adjust the modulation amplitude of the light source based an the detected pressure. The analysis of the light detector signal happens for example at the second harmonic of the modulation frequency. Measuring the pressure and adapting the modulation amplitude as proposed can compensate the pressure dependency of the measuring signal. However, this requires the use of a pressure sensor and a pressure calibration routine.

With reference to the aforementioned prior art it is an object of the present invention to provide an improved method and an enhanced apparatus for accurately measuring a concentration of a target gas without compensating either pressure variations of the gas or the atmospheric pressure changes.

According to the invention this object is solved by a method and by an apparatus for appliance of this method as described herein.

The suggested method is based on optimizing the wavelength modulation amplitude of the laser to minimum pressure dependency. The apparatus is adapted for detecting the concentration of a target gas in compliance with the suggested method.

In detail, the inventive method for detecting the concentration of a target gas comprises the following steps:

Emitting wavelength modulated light from a laser light source which wavelength range covers the absorption resonance of the target gas, detecting an intensity of the laser light at multiple pressures after the light has passed the target gas, then determining a point of lowest pressure dependency of a concentration equivalent signal, preferably peak height or peak-valley height of a measuring signal on a light detector, in function of the wavelength modulation amplitude of the laser light, adjusting a working point of the wavelength modulation amplitude for a selected pressure range to lowest pressure dependency of the measuring signal based on the determined points of lowest pressure dependency of the concentration equivalent signal, and after this, detecting the reduced pressure dependent intensity of the wavelength amplitude modulated light behind the target gas and demodulating the measuring signal for computing the concentration of the target gas. In doing so a measuring frequency of the modulation frequency f is used, n being a positive integer, preferably 2.

SUMMARY OF THE INVENTION

According to the present invention within one embodiment of method the point of minimal pressure dependency is measured in a first apparatus and then applied on other apparatus measuring the similar mixtures of gas(es) or within another embodiment the point of minimal pressure dependency is found by a simulation based on experimental data in database or literature instead of directly measured values.

Within a preferred embodiment of the invention the method uses a usual electronic control unit to control the light source and to process the measuring signal of the light detector. The control unit comprises a lock-in amplifier and a microprocessor with a special program that allows beside other parameters to adjust the wavelength modulation amplitude and to compute the concentration level of the target gas.

Corresponding to a further embodiment it proves favorable to provide the electronic control unit for changing the wavelength modulation amplitude of the laser light between working point for maximum sensitivity and the working point for minimal pressure dependency.

Furthermore, in another embodiment it is particularly favorable to influence the working point of the wavelength modulation amplitude for lowest pressure dependency by a temperature sensor connected to the control unit.

The signal is not only affected by the pressure, but also by background gases that can either act on the signal of the target gas by interference (modulated peak of background gas(es) is/are close to the target gas and the shape of the peaks interfere with each other) and/or broaden the line width by collision broadening. This can be compensated by a proper calibration taking into account the cross sensitivity and interference to other gases. However, both effects are sensitive to pressure variations. The proposed method can be applied to background gases as well, which allows removing any (or at least reducing the) pressure dependency of the cross-interference parameters of background gases.

Besides it makes sense to store the working points for different pressure ranges in data storage of the electronic control unit, so that said data can be recalled for detecting the concentration of a target gas in view of an estimated or measured gas pressure.

Generally said method can use any coherent light source with enough spectral purity, which could be for example a tunable diode laser, a gas laser, a solid state laser, a quantum cascade laser, an interband cascade laser, a source based on optical parametric frequency conversion, and a light detector with a high enough sensitivity and time resolution, which could be for example a Si detector, a Ge detector, InGaAs detector, an InAs detector, or a Mercury-Cadmium-Telluride detector. Moreover an effective path length between the light source and light detector can be increased by using a Herriott cell, a White cell, a cell with at least one reflecting surface, or a cell without any reflecting surfaces being arranged between the light source and the light detector.

The inventive apparatus is adapted to perform the suggested method. Thus, the apparatus utilizes a modulated tunable laser source allowing to scan over the absorption line of the target gas, a detector that detects the intensity of laser radiation (dc and at multiples of the modulation frequency) that passed through the gas and a control electronic. The laser source may be for example a tunable diode laser, a gas laser, a solid-state laser, a quantum cascade laser, an interband cascade laser, a source based on optical parametric frequency conversion. The detector may be for example a Si detector, a Ge detector, InGaAs detector, an InAs detector, a Mercury-Cadmium-Telluride detector. A sample cell can be used to increase the effective path length between laser source and detector, as for example, a Herriott cell, a White cell, a cell with at least one reflecting surface, a cell without any reflecting surfaces. The control electronic includes a lock-in amplifier and a microprocessor with a program that allows to adjust the modulation amplitude and to compute the concentration level of the target gas.

Depending on the application, the gas pressure may vary considerably around the operation point and may affect the measured concentration level. The goal was to reduce the dependence of such pressure variations and those from atmospheric pressure changes on the accuracy of the concentration level. The new method presents several benefits, for example a simpler calibration, no need of pressure correction, reduced effects of flow rate in a flow-through measurement cell, reduced effect of atmospheric pressure change, increased working altitude range in the specifications.

Below, the invention is explained in detail with reference to an embodiment shown in the drawings. Other features and advantages of the subject matter described herein will be apparent from the description and drawings, and from the claims. In different implementations of the invention, the individual characteristics may be implemented either by themselves or in combinations of several. The following figures show in

DETAILED DESCRIPTION OF THE INVENTION

Figure 1:
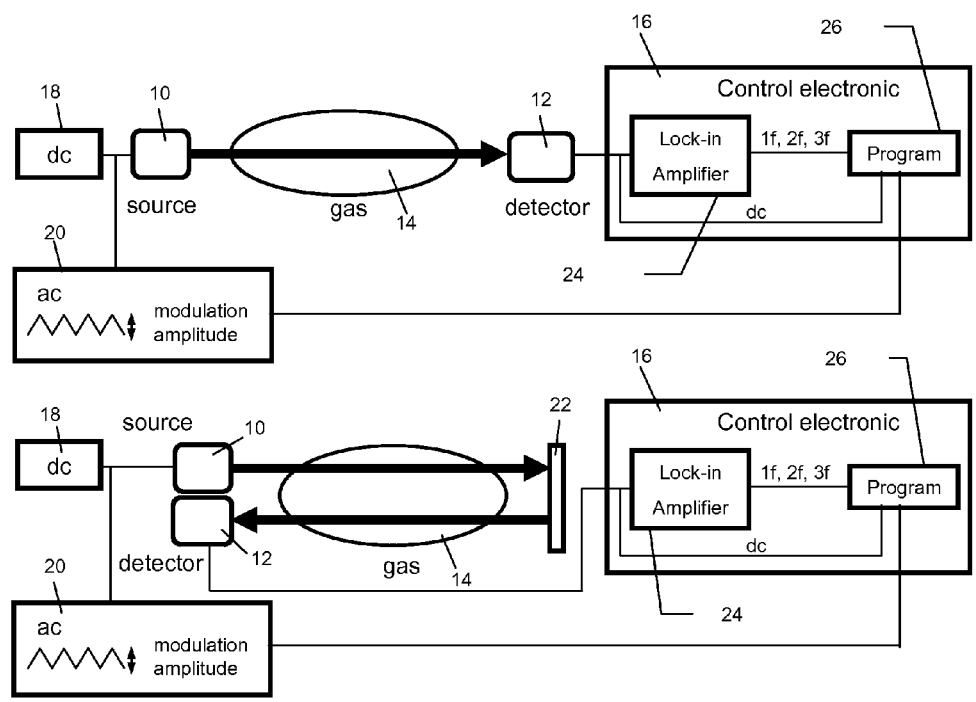
FIG. 1 a schematic drawing of two possible apparatus arrangements for measuring gas concentrations.

FIG. 1 shows the schematic drawings of two possible configurations of an apparatus for measuring the concentration of a gas. The apparatus in the upper drawing includes a tunable laser source 10 driven by a dc current source 18 and ac current source 20, a gas 14, a detector 12, a control unit 16 that comprises a lock-in amplifier 24 and a microprocessor 26 with a program. The second apparatus, shown in the lower drawing, shows the same elements as the upper drawing, but with a reflecting optic 22. The ac current source 20 comprises a function generator where the modulation amplitude can be adjusted by the control electronic 16. The laser source 10 might be a tunable diode laser, a gas laser, a solid state laser, a quantum cascade laser, an interband cascade laser, or a source based on optical parametric frequency conversion. The detector 12 might be a Si detector, a Ge detector, InGaAs detector, an InAs detector, or a Mercury-Cadmium-Telluride detector. A sample cell can be used to increase the effective path length between laser source and detector, as for example, a Herriott cell, a White cell, a cell with at least one reflecting surface, or a cell without any reflecting surfaces. The control electronic 16 includes a lock-in amplifier and a microprocessor with a program that allows, beside other parameters, to adjust the wavelength modulation amplitude and to compute the concentration level of the target gas. Optional beam shaping elements, like lenses, can be used in those apparatuses not shown in the drawing.

The laser wavelength is tuned over one or several absorption lines of the target gas, which allows performing tunable diode laser spectroscopy (TDLS) with this apparatus. In case of relevant cross sensitivity of the target gas to one or several background gases, the same laser source can be utilized to scan over one or several absorption lines of one or several background gases. Emission wavelength of the laser can be either changed by direct temperature tuning or indirectly by changing the laser's dc drive current. In addition, the lasing wavelength is modulated by the ac current source which produces a certain waveform, for example a sine or triangular waveform, that reproduces itself at a certain frequency f and amplitude. The wavelength modulation is accompanied by an intensity modulation, which is normally weaker in VCSELs (vertical cavity surface emitting lasers) compared with edge-emitting lasers. Both, wavelength and intensity modulation, result in a modulated signal on the detector. Using a lock-in technique, multiple of the modulation frequency f can be extracted which allows the realization of a very sensitive absorption spectroscopy measurement technique known as wavelength modulation spectroscopy (WMS).

Figure 2:
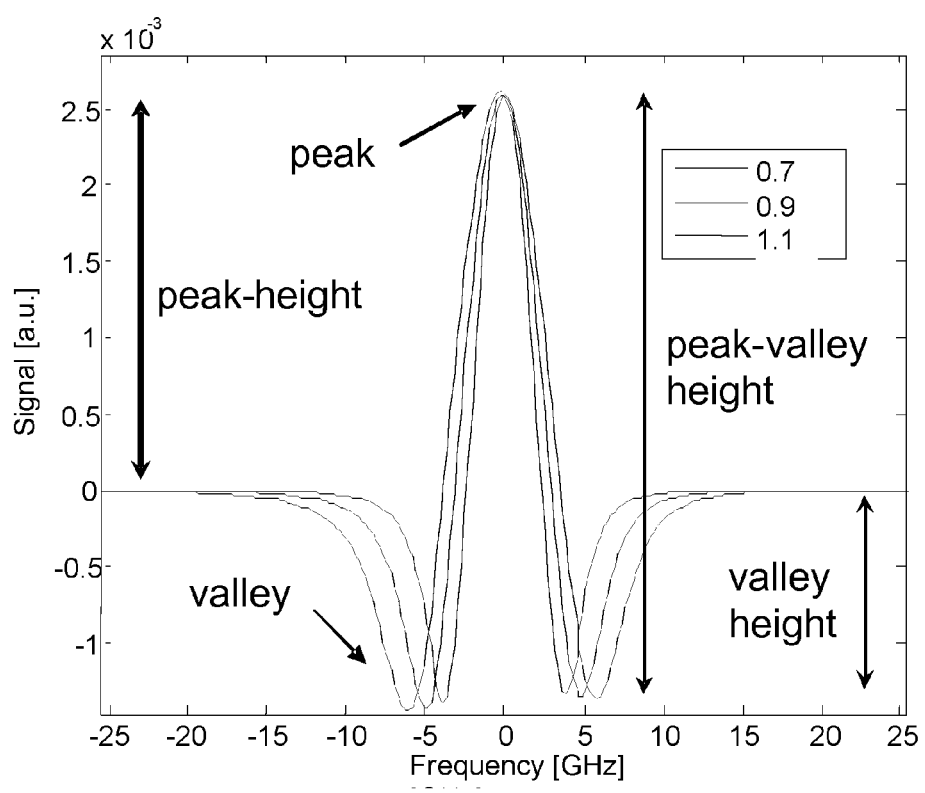
FIG. 2 a graph of computed signals at the second harmonic modulation frequency for different pressures corresponding to the absorption peaks in FIG. 4.
Figure 3:
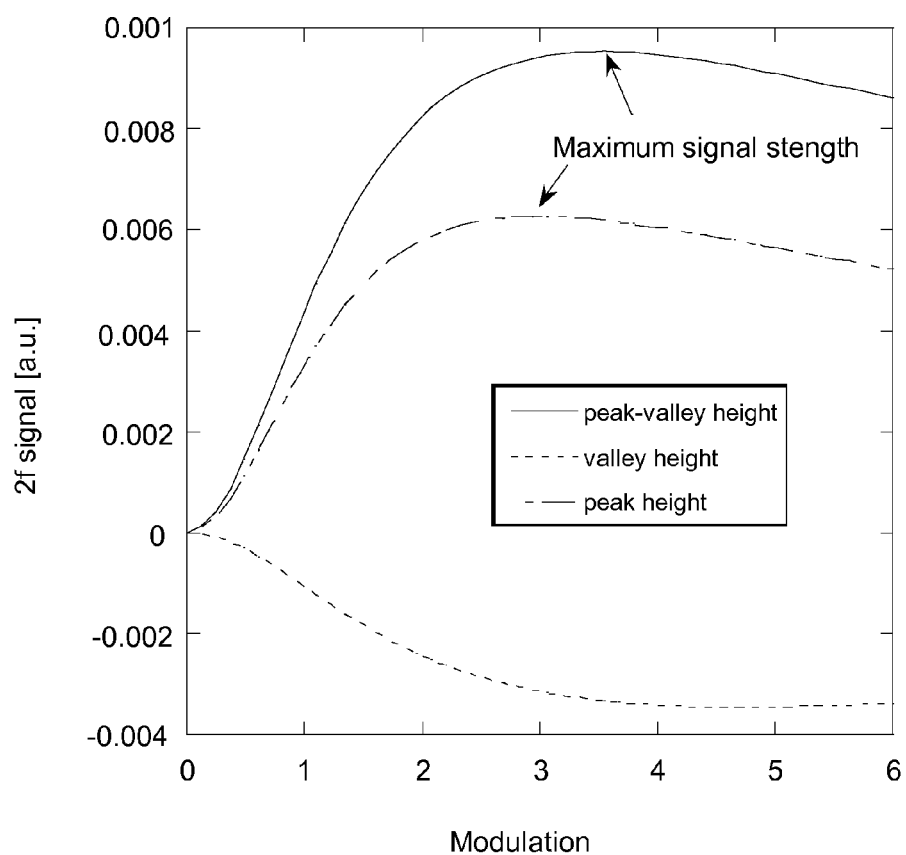
FIG. 3 a graph of computed signal at the second harmonic frequency 2f versus modulation index for peak-height, valley-height and peak-valley height.

The signal of a multiple of the modulation frequency, e.g. 1f, 2f, 3f, from the lock-in is used to calibrate the sensor for a certain gas concentration. Alternatively, the harmonic signal after lock-in is normalized by the dc component and this ratio is used for the calibration. For example, the simulated 2f-signal in FIG. 2 shows a maximum in the center and two local minima on either side. The peak-height, the valley-height or the distance between the peak and valley, either one or both of the valleys, (peak-valley height) can be used as concentration equivalent signal for the calibration. Peak-height, peak-valley and peak-valley-height change with the wavelength modulation amplitude A. The modulation amplitude A for maximum signal (see FIG. 3) is optimized in order to obtain the best signal to noise level. The maximum signal is reached for a certain modulation index m, which is defined as a multiple of the FWHM of the absorption line width $\Delta v$:

$$m = \frac{A}{\Delta v}$$

The modulation index at which maximum signal is reached is depending on the waveform of the modulation signal. For a triangular-shaped waveform the maximum signals are reached for m=2.8 for peak height and m=3.5 for peak-valley-height.

Figure 4:
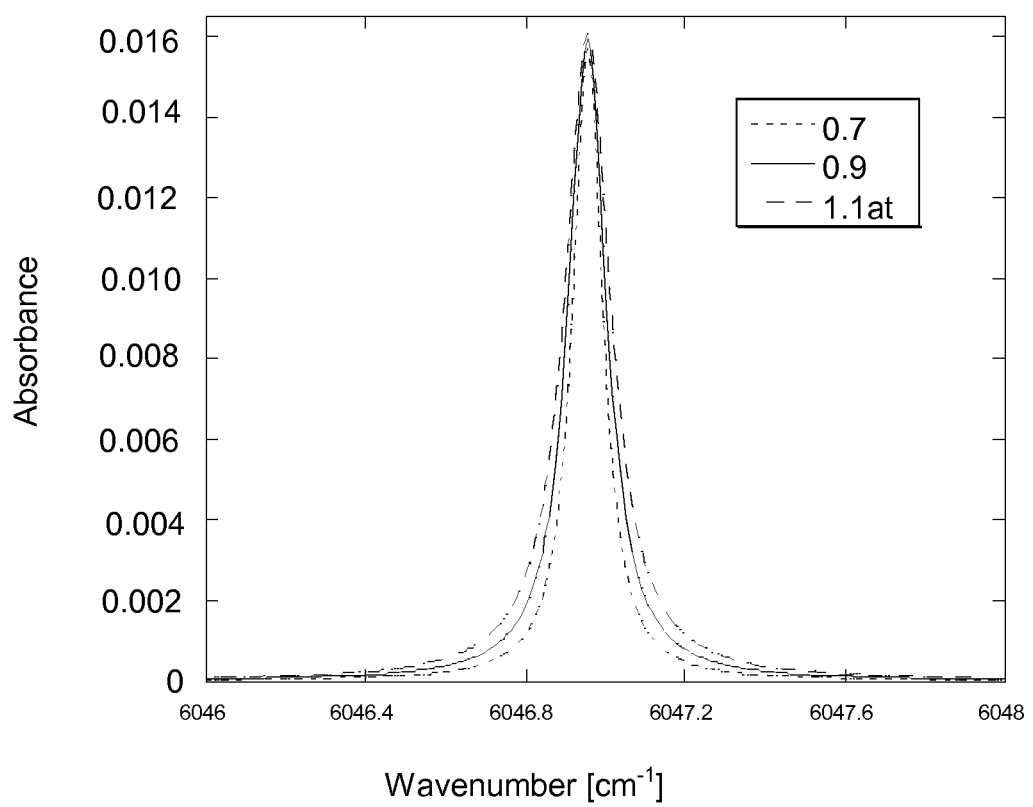
FIG. 4 a graph of calculated absorbance of 1000 ppm $CH_4$ in air at different pressures assuming a Lorentzian lineshape and using the parameters given in the HITRAN 2008 database.
Figure 5:
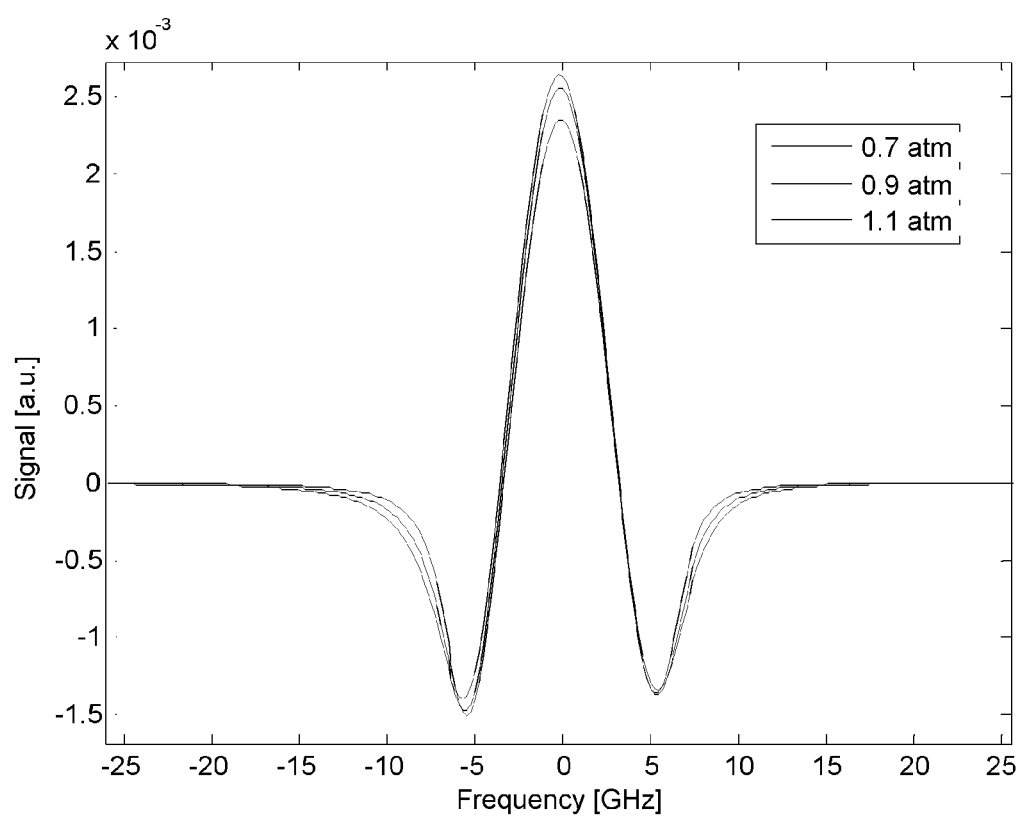
FIG. 5 a graph of computed signals at the second harmonic frequency corresponding to different pressures at fixed modulation index.
Figure 6:
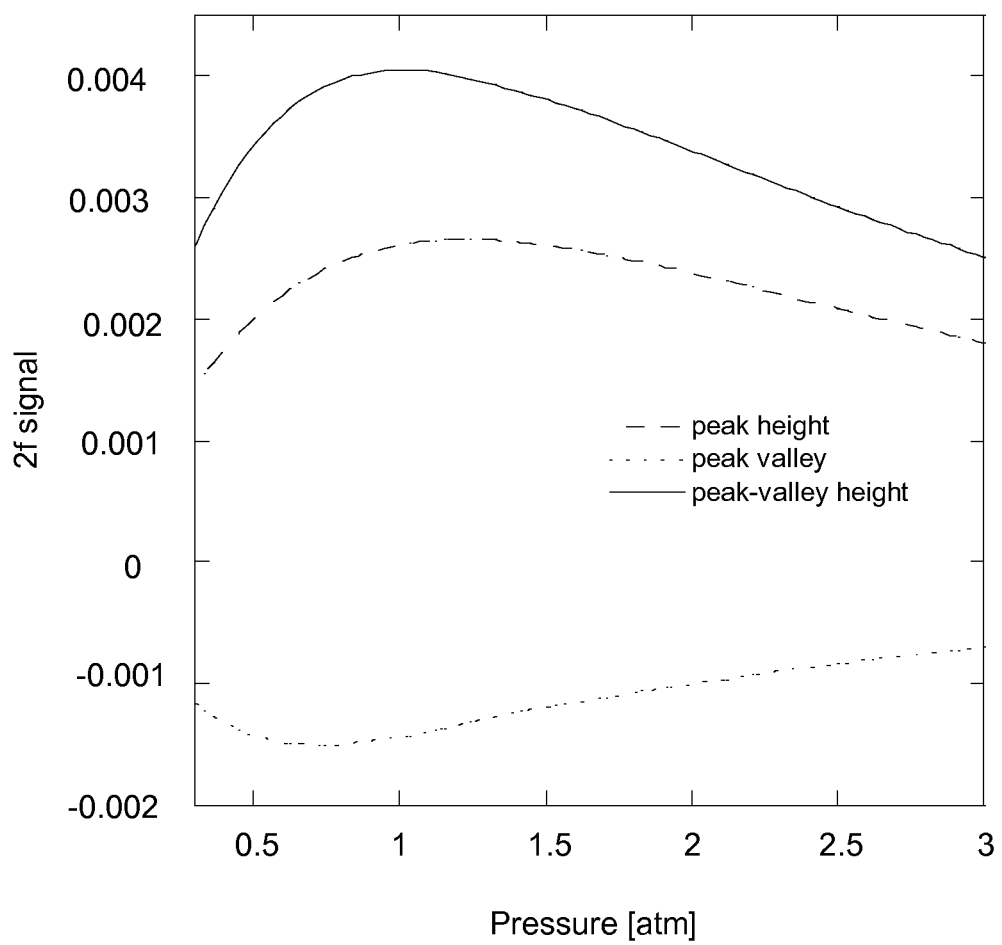
FIG. 6 a graph of computed signals at the second harmonic frequency versus gas pressure.

Depending on the application, the gas pressure may vary considerably around the operation point. FIG. 4 depicts for different pressures the simulated absorption line of methane ($CH_4$) around a wave number of 6046.9 $cm^{-1}$. As seen, the pressure dependency of the peak absorbance is relatively weak. The corresponding 2f-signals are shown in FIG. 2 which were computed using the same modulation index (not the same amplitude). It is apparent that the valley-peak height of the 2f-signal only weakly depends on pressure. Unfortunately, WMS is very sensitive to changes in the modulation index itself. This is shown in FIG. 5 where the modulation amplitude is fixed (modulation index changes). A change of the pressure results in a variation of the signal. Since the FWHM of the gas is inversely proportional to the pressure, a change of pressure will result in a change of the modulation index (when working at a fixed modulation amplitude) and as a consequence, in inaccuracy in the measured gas concentration. FIG. 6 shows the 2f-signals as function of pressure, assuming a Lorentzian line shape of the absorption peak.

Figure 7:
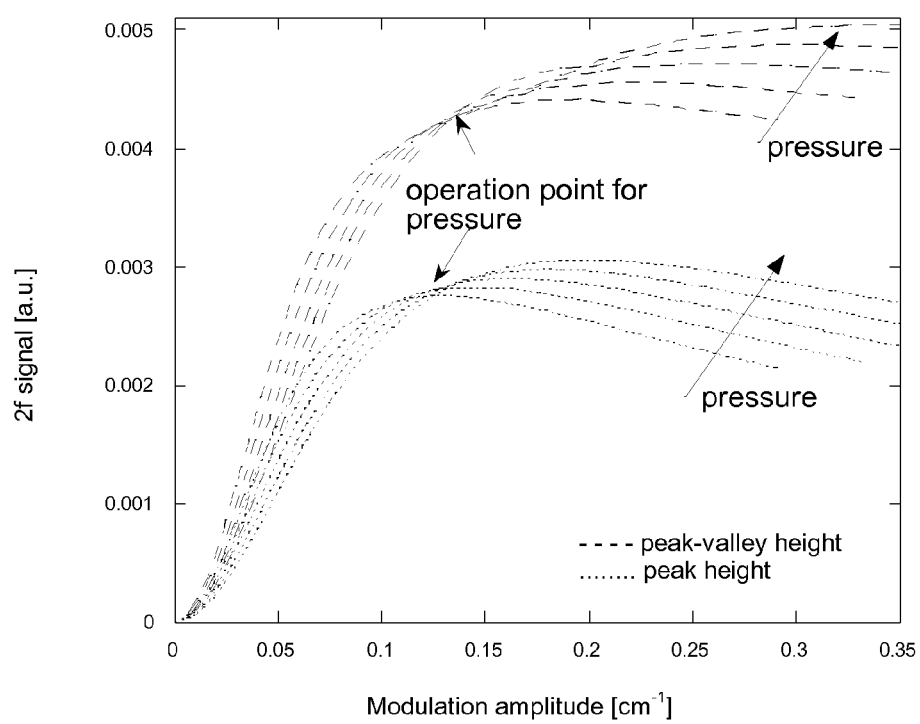
FIG. 7 a graph of computed signals at the second harmonic frequency versus modulation amplitude at different pressures between 700 and 1100 h Pa.

In FIG. 7, the 2f-signals are computed for different modulation amplitudes and pressures. It is visible, that there exists a crossing point at a certain modulation amplitude at which the deviation of the 2f-signals for different pressures is minimal. The invention proposes to optimize the modulation amplitude for minimum pressure dependency. Setting the modulation amplitude of the sensor to this crossing point, or close to this point, results that the concentration is invariant, or at least less affected, to pressure variations.

Figure 8:
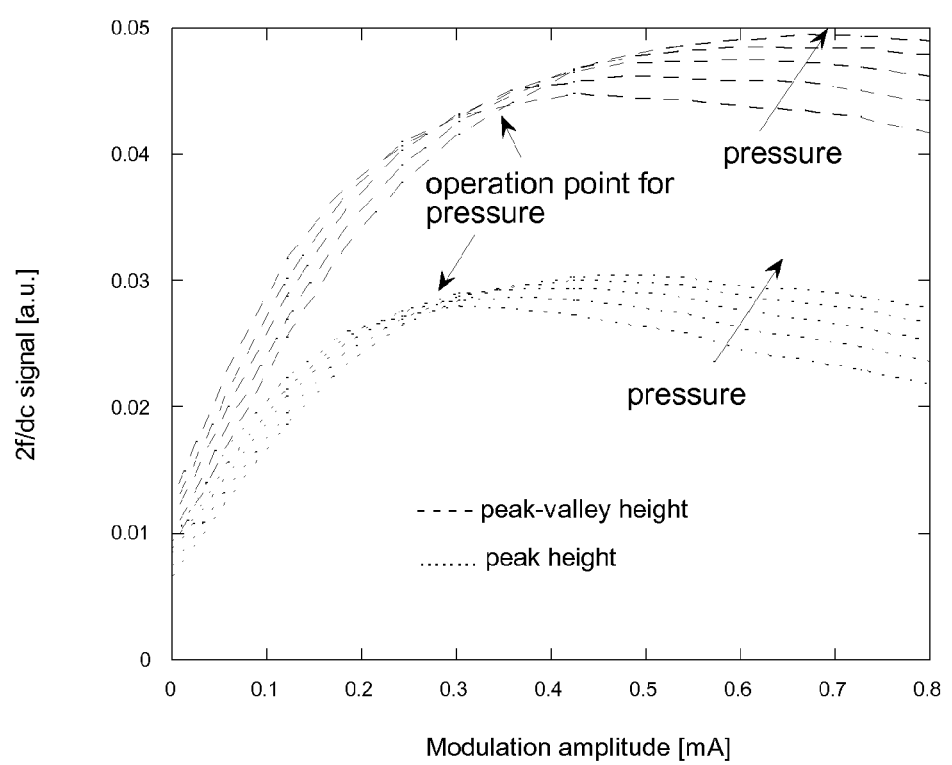
FIG. 8 a graph of measured signals at the second harmonic frequency normalized by the dc signal versus modulation amplitude at different pressures between 700 and 1100 hPa.
Figure 9:
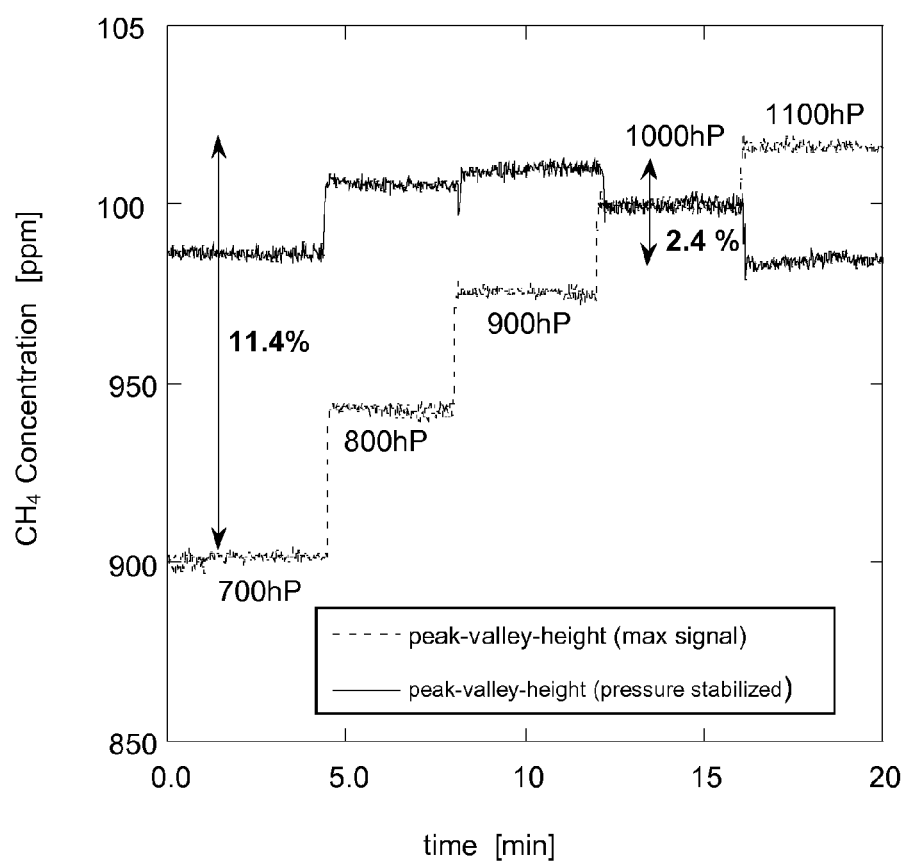
FIG. 9 a graph of measured concentration of $CH_4$ at different pressures with different working point of the wavelength modulation amplitude.
Figure 10:
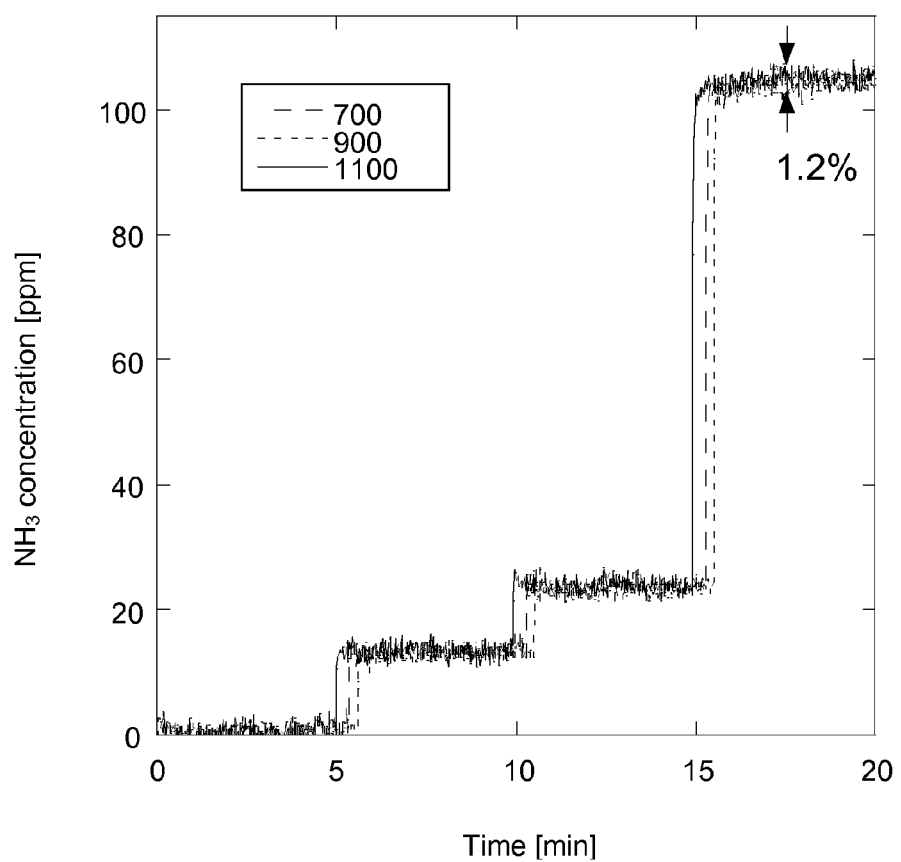
FIG. 10 a graph of measured concentration profile of $NH_3$ at different pressures.

FIG. 8 shows experimental data of the measurement of 1000 ppm $CH_4$ in $N_2$, where the 2f-signal, normalized by the dc signal, is plotted versus modulation amplitude for different pressures between 700 and 1100 hPa. The signal from the detector before the lock-in, or the dc signal after lock-in operation can be used as dc signal. Minimum pressure dependency is achieved at a modulation amplitude of 0.355 mA for the peak-valley height and 0.28 mA for peak-height, respectively. This translates into pressure variations of only 2.4 to 2.8%, respectively. FIG. 9 shows a comparison of the two possible measurements modes. In case the sensor is optimized for maximum signal, one ends up with a variation in concentration of 11.4%. In contrast, the method which is optimized for lowest pressure dependency results in a concentration variation of only 2.4% within the same pressure range between 700 and 1100 hPa. It is possible to use both methods for the same sensor, allowing operating it in applications where the pressure is controlled, benefiting from a better signal-to-noise ratio, or in applications where the pressure is not known and/or fluctuations in the gas flow are present requiring to be insensitive to pressure variations. The method of reducing the pressure dependency was also applied to other gases. FIG. 10 shows the measurement of different $NH_3$ concentrations that were recorded at different pressures. From this data it is possible to derive a pressure dependency of the concentration of only 1.2%, demonstrating that the proposed method by itself is almost inert to the pressure variations around the operation point and allows for omitting a pressure sensor. Furthermore, it is not necessary to calibrate the apparatus for different pressures.

The modulation amplitude at which minimal pressure dependency exists depends itself on the concentration C since the line-broadening is a linear combination of self broadening and broadening due to the background gas which themselves are depending on the concentration:

$$\Delta \tilde{\nu} \propto g_{self} C + g_{background}(1-C)$$

Figure 11:
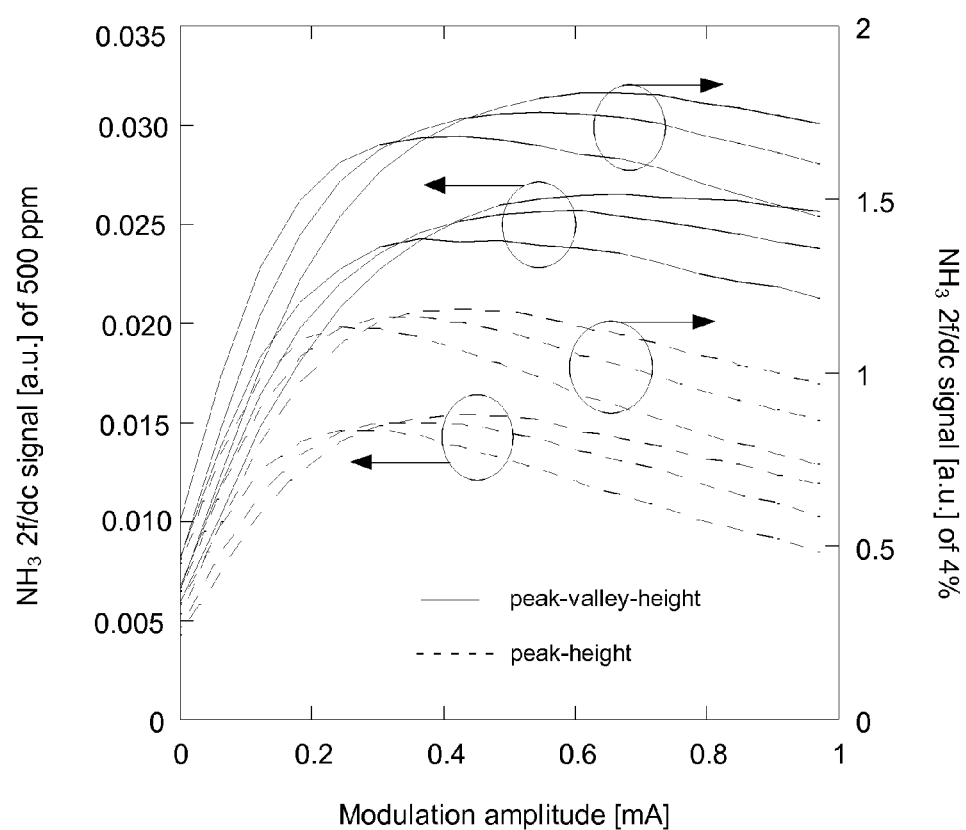
FIG. 11 a graph of computation of the effect of self-broadening on the line width.

At low concentration, the broadening due to the background gas dominates. At higher concentrations, normally in the percentage range, self-broadening contributes to the line width. Fortunately, this effect should be small. For example, an increase of the concentration of $CH_4$ in air from 500 ppm to 4% should result in an increase of only 1.3% of the line width. This would shift the modulation amplitude by the same factor to higher values. FIG. 11 shows experimental data of $CH_4$ in $N_2$, showing that the effect of self-broadening can be neglected as long as the concentration of the target gas is not exceeding few percentages. Optional, for large concentration levels, one can use the measured concentration level to adapt the modulation amplitude for optimum crossing point.

The gas line width is not only determined by self- and background broadening but also by the temperature of the gas:

$$\Delta \nu_l \propto \left(\frac{296K}{T[K]}\right)^{n_{air}}$$

Figure 12:
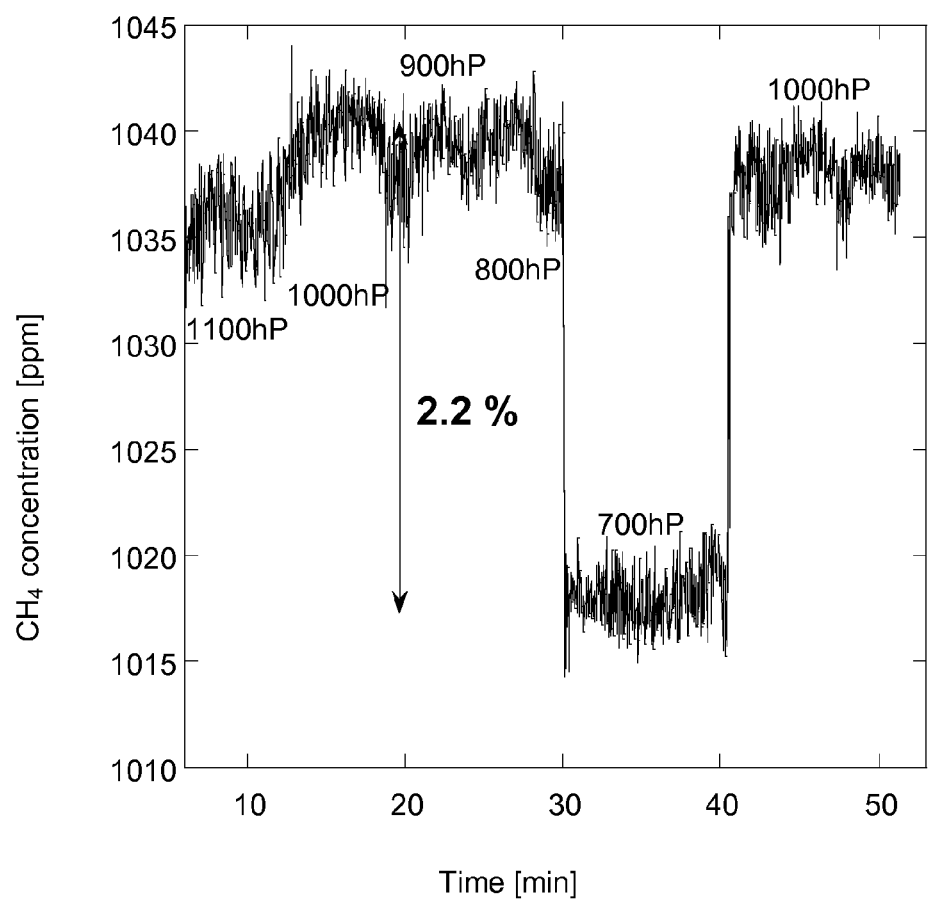
FIG. 12 a graph of measurement of a fixed concentration at different pressures.
Figure 13:
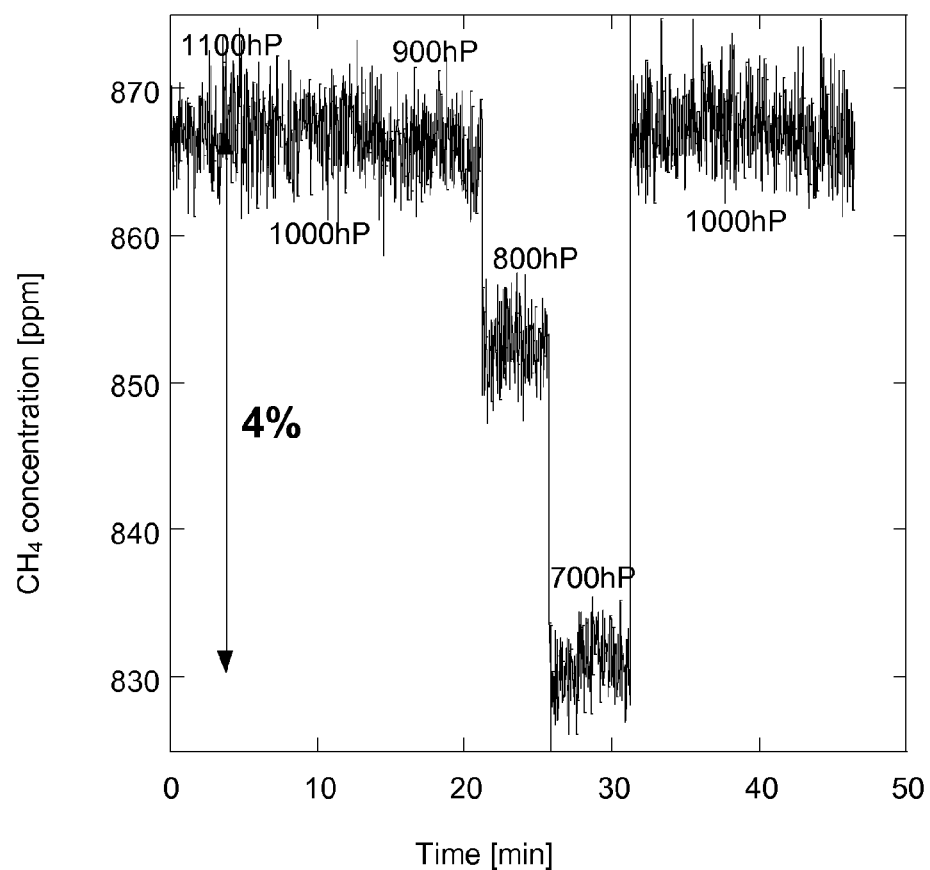
FIG. 13 a graph of measurement of the concentration at different pressures at a temperature of 65° C.

Where, in most cases, the factor is $n_{air} \neq 0.5$-$0.8$. Increasing the temperature from the calibration temperature will decrease the line width of the gas line and consequently shift the optimum crossing point to lower modulation amplitude. Correspondingly, a decrease in temperature results in an optimum modulation amplitude, which is larger. The effect of this shift is depending on the slope of the curves; see for example in FIG. 8. FIG. 12 depicts the calibration profile that shows a pressure dependency of the concentration of 2.2%, which was measured at the temperature for which the modulation amplitude was optimized. The pressure dependency of the concentration increases to only 4% when the temperature is increased from 25° C. to 65° C., which is shown in FIG. 13. Optional it is possible to use a temperature sensor to adapt the modulation amplitude for optimum crossing point and therefore, lowest pressure dependency of the concentration.

Figure 14:
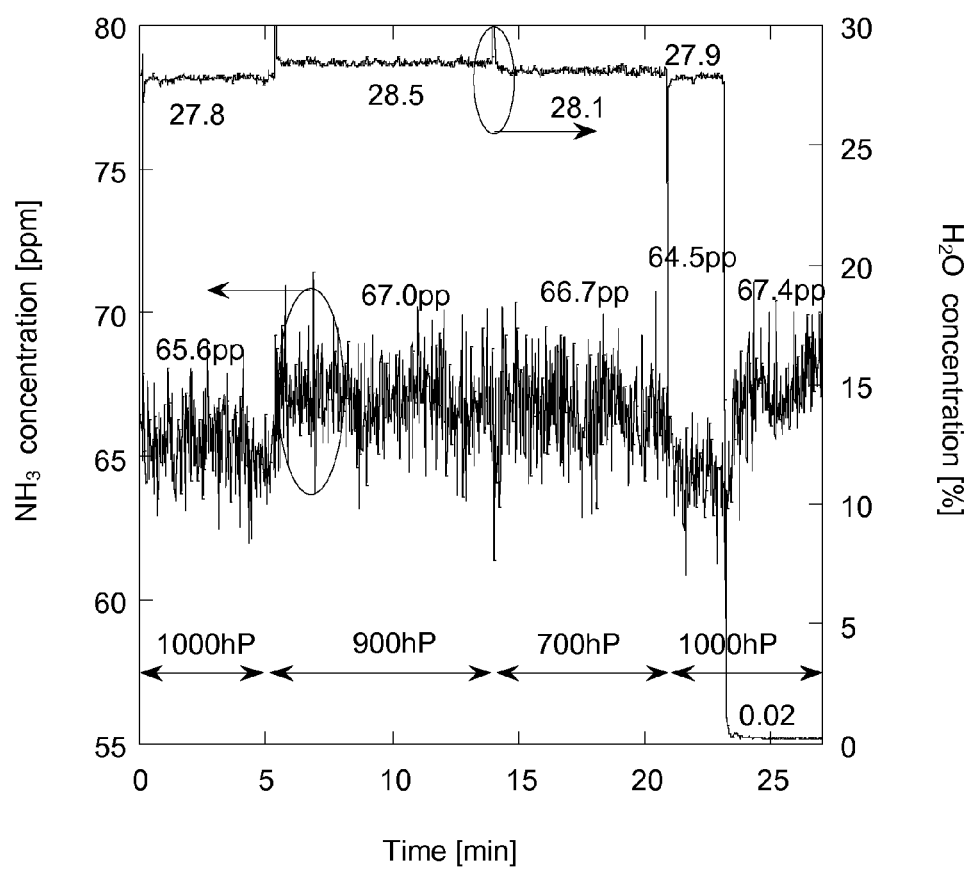
FIG. 14 a graph of measurement of a fixed concentration at different pressures with or without high level of humidity.

The signal is not only affected by pressure fluctuations, temperature variations and self-broadening, but also by one or several other gas species present in the background gas or the background gas itself that can either act on the signal of the target gas by interference (modulated signal of other gas species/background gas(es) is/are close to the target gas and the shape of the peaks interfere with each other) and/or broaden the line width by collision broadening. This can be compensated by a proper calibration taking into account the cross sensitivity and interference to other gases. However, both effects are sensitive to pressure variations. The same method of making the target gas insensitive to pressure variations can be applied to background gases, which allows for removing any (or at least reducing the) pressure dependency of the cross-interference parameters of background gases. FIG. 14 shows almost no effect of pressure variations on the concentration, although a high amount of humidity is present in the background gas.

Although the invention has been shown and described with respect to certain preferred embodiments, it is obvious that equivalents and modifications will occur to others skilled in the art upon the reading and understanding of the specification. The present invention includes all such equivalents and modifications, and is limited only by the scope of the following claims.

The invention claimed is:

1. A method for detecting a concentration of a target gas, the method comprising:
   emitting wavelength modulated light by a laser light source, wherein an emitted wavelength range covers at least one absorption line of the target gas;
   detecting with a light detector a detector signal of light at various pressures of the gas mixture after the light has passed the target gas; and with an electronic control unit performing the steps of:
   demodulating the detector signal at a fundamental or harmonic frequency of wavelength modulation and extracting a concentration equivalent signal comprising a peak-valley or peak height;
   determining a point of lowest pressure dependency of the concentration equivalent signal in function of a wavelength modulation amplitude; and
   adjusting a working point of wavelength modulation amplitude to the determined point of lowest pressure dependency for a selected pressure range for the following gas concentration measurements,
   wherein a measuring frequency nf of the modulation frequency f is used, n being a positive integer.

2. The method as described in claim 1, wherein the point of minimal pressure dependency is measured in a first apparatus and then applied on other apparatus measuring the similar mixtures of gas(es).

3. The method as described in claim 1, wherein the point of minimal pressure dependency is found by a simulation based on experimental data in database or literature instead of directly measured values.

4. The method as in claim 1, wherein using an electronic control unit to control the laser light source and to process a measuring signal of the light detector, wherein the control unit comprises a microprocessor for adjusting beside other parameters the wavelength modulation amplitude and to compute a concentration level of the target gas.

5. The method as in claim 4, wherein normalizing the demodulated signal by a single dc-value or by two of more dc-values being arithmetically combined, where the dc-value (s) can be either the dc-value(s) before or after a lock-in operation.

6. The method as in claim 4, wherein influencing a working point of the wavelength modulation amplitude for lowest pressure dependency by a temperature sensor connected to the electronic control unit.

7. The method as claimed in claim 1, wherein storing the working points for different pressure ranges in a data storage of the electronic control unit and by recalling a certain range in view of an estimated or measured gas concentration.

8. The method as claimed in claim 1, wherein changing the wavelength modulation amplitude of laser light between maximum sensitivity and minimal pressure dependency.

9. The method as claimed in claim 1 applied to other gas species cross-interfering with a first gas species.

10. The method as claimed in claim 1, wherein n is 2.

11. An apparatus for detecting a concentration of a target gas, the apparatus comprising:

a tunable laser source that emits wavelength modulated light at wavelengths substantially equal to at least one absorption line of the target gas;

a detector that detects an intensity of light at multiple pressures of the target gas after the light has passed the target gas; and an electronic control unit configured to:

determine a point of lowest pressure dependency of a concentration equivalent signal comprising a peak height or a peak-valley height, of a measuring signal of a light detector in dependency of a wavelength modulation amplitude of the wavelength modulated light, wherein a measuring frequency nf of the modulation frequency f is used, n being a positive integer;

adjust a working point of wavelength modulation amplitude for a selected pressure range to lowest pressure dependency of the measuring signal based on the determined points of lowest pressure dependency of the concentration equivalent signal; and detect reduced pressure dependent intensity of the wavelength modulated light behind the target gas and demodulating the measuring signal for computing the concentration of the target gas.

12. The apparatus as claimed in claim 11, wherein the electronic control unit further is configured to control the tunable laser source and to process the measuring signal of the light detector, the control unit comprising a lock-in amplifier and a microprocessor, wherein the microprocessor is adapted to adjust beside other parameters the wavelength modulation amplitude and to compute the concentration level of the target gas.

13. The apparatus as claimed in claim 11, wherein the electronic control unit further is configured to normalize the demodulated signal by a single dc-value or by two of more dc-values being arithmetically combined, where the dc-value(s) can be either the dc-value(s) before or after a lock-in operation.

14. The apparatus as claimed in claim 11, comprising a temperature sensor connected to the electronic control unit, adapted to influence a working point of a modulation width for lowest pressure dependency.

15. The apparatus as claimed in claim 11, comprising a data storage unit to store working points for different pressure ranges, wherein the electronic control unit further is configured to store in the data storage unit said working points and to recall a certain working point in view of an estimated or a measured gas concentration.

16. The apparatus as claimed in claim 11, wherein the electronic control unit further is configured to change the wavelength modulation amplitude of the wavelength modulated light between maximum sensitivity and minimal pressure dependency.

17. The apparatus as claimed in claim 11, wherein n is 2.

* * * * *